US012558525B2

(12) United States Patent
Henke et al.

(10) Patent No.: US 12,558,525 B2
(45) Date of Patent: Feb. 24, 2026

(54) DEVICE AND METHOD FOR PRODUCING A PATCH WHICH HAS A PLURALITY OF MICROSTRUCTURES

(71) Applicant: LTS Lohmann Therapie-Systeme AG, Andernach (DE)

(72) Inventors: Stefan Henke, Kirchen (DE); Hagen Trommer, Leipzig (DE); Sebastian Scherr, Neuhäusel (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 778 days.

(21) Appl. No.: 17/917,347

(22) PCT Filed: Mar. 29, 2021

(86) PCT No.: PCT/EP2021/058153
§ 371 (c)(1),
(2) Date: Oct. 6, 2022

(87) PCT Pub. No.: WO2021/204578
PCT Pub. Date: Oct. 14, 2021

(65) Prior Publication Data
US 2023/0149681 A1 May 18, 2023

(30) Foreign Application Priority Data
Apr. 7, 2020 (DE) ..................... 10 2020 109 626.7

(51) Int. Cl.
*A61M 37/00* (2006.01)
(52) U.S. Cl.
CPC . *A61M 37/0015* (2013.01); *A61M 2037/0053* (2013.01); *A61M 2207/10* (2013.01)

(58) Field of Classification Search
CPC ...... A61M 37/0015; A61M 2037/0053; A61M 2207/10
See application file for complete search history.

(56) References Cited

U.S. PATENT DOCUMENTS

| | | | |
|---|---|---|---|
| 2008/0275400 A1 | 11/2008 | Ferguson | |
| 2016/0082626 A1* | 3/2016 | Kato | ....................... B29C 43/34 425/127 |

(Continued)

FOREIGN PATENT DOCUMENTS

| | | |
|---|---|---|
| CN | 106727273 A | 5/2017 |
| JP | 2008245955 A | 10/2008 |

(Continued)

*Primary Examiner* — Galen H Hauth
*Assistant Examiner* — Erica Hartsell Funk
(74) *Attorney, Agent, or Firm* — The Webb Law Firm

(57) ABSTRACT

A device for producing a patch which includes a plurality of microstructures has at least one die. The die is used to produce a microstructure and has a plurality of depressions for this purpose. Additionally, a support layer, which is provided with an adhesive layer, is provided. In a preferred embodiment, it is possible to move the microstructure formed in the die in the direction of the support layer using a lifting device such that said microstructure adheres to the face of the support layer, which is provided with the adhesive layer. For example, by carrying out a corresponding method multiple times, multiple microstructures can be provided on the support layer adjacently to one another. Optionally, multiple dies can also be provided so that multiple microstructures can be simultaneously arranged on the support layer.

8 Claims, 1 Drawing Sheet

(56)                    References Cited

U.S. PATENT DOCUMENTS

2018/0311486  A1     11/2018  Park
2020/0009767  A1*    1/2020   Li  ........................... B29C 39/24

FOREIGN PATENT DOCUMENTS

| | | | |
|---|---|---|---|
| JP | 2013244341 | A | 12/2012 |
| JP | 201667723 | A | 5/2016 |
| JP | 201738904 | A | 2/2017 |
| KR | 1020180080476 | A | 7/2018 |
| WO | 2017007156 | A1 | 1/2017 |

* cited by examiner

1

DEVICE AND METHOD FOR PRODUCING A PATCH WHICH HAS A PLURALITY OF MICROSTRUCTURES

CROSS-REFERENCE TO RELATED APPLICATIONS

This application is the United States national phase of International Application No. PCT/EP2021/058153 filed Mar. 29, 2021, and claims priority to German Patent Application No. 10 2020 109 626.7 filed Apr. 7, 2020, the disclosures of which are hereby incorporated by reference in their entirety.

BACKGROUND OF THE DISCLOSURE

Field of the Disclosure

The disclosure relates to a device as well as a method for producing a patch comprising multiple microstructures, in particular microneedles.

Description of Related Art

The microstructures to be produced are preferably microneedles, which are in particular arranged in a microneedle array. Microneedles are used for releasing active agents directly into the skin, also referred to as intradermal administration. For this purpose, the microneedles are of precisely such a length for penetrating only into the outer skin layers, but preferably not reaching nerves and blood vessels, and thus leaving these uninjured. Nonetheless, microneedles produce small holes in the upper skin layers, as a result of which the active agent absorption is significantly increased compared with a purely external application of active agents onto the skin.

Microneedle arrays, which comprise a plurality of microneedles, for example attached to a support surface, can be used for short-term administration or long-term application. A preferred possibility for active agent discharge from the microneedles into the skin consists in active agent-containing regions of the microneedles or the entire microneedle dissolving or detaching, and thereby being taken up by the body via the skin. For this purpose, the microneedles are in particular produced, at least in part, from waterless materials. In addition to the direct active agent discharge via the microneedles themselves, it is also possible for the microneedles to comprise pores or voids or are formed as hollow needles, in order to thereby allow for active agent discharge onto the skin. Furthermore, microneedles can also be inherently active agent-free. In this case for example external application of the active agent to the outside of the microneedles can then take place, or an active agent-containing substance can be applied to the corresponding skin location only after removal of the microneedles from the skin, in order to administer active agents of this kind by means of using microneedles.

In a known method for producing microneedle arrays, a liquid containing the corresponding active agent, or a corresponding formulation, is poured onto a die. The die, produced in particular from silicone, comprises a plurality of cavities which form the needles. The size of microneedle arrays is dependent on the size of the dies. This is limited, in particular in order to be able to expediently perform shaping of the microneedle array. Typical sizes of such dies are in the range of 1 to 2 cm².

2

In the case of larger applications, it is therefore problematic that a plurality of individual microneedle arrays have to be applied to the skin.

SUMMARY OF THE DISCLOSURE

The object of the disclosure is that of providing a device and a method for producing a patch comprising a plurality of microstructures.

The object is achieved according to the disclosure by a device and a method as described herein.

The disclosure relates to a device for producing a patch comprising a plurality of microstructures. The microstructures are in particular microneedle arrays comprising a plurality of needles. The device according to the disclosure comprises at least one die which is produced for example from silicon or another in particular resilient material. The die comprises a plurality of depressions which serve for producing the microstructure, in particular of the microneedle array. In this case, the depressions are formed in particular as pyramids having a rectangular or square cross-section, or conically having a round cross-section. The device further comprises a support layer provided with an adhesive layer. For this purpose, the device can comprise a retaining device which retains the corresponding support layer. The support layer is used for receiving a plurality of microstructures, which are retained by the adhesive layer.

According to the disclosure, the device comprises a lifting device. By means of the lifting device, it is possible to perform a relative movement, in particular in the horizontal direction, between the at least one die and the support layer. This makes it possible to press a microneedle array, arranged in the die, against the adhesive layer of the support layer, such that the microneedle array adheres to the support layer, and as a result can be demolded from the die, in particular by moving the die away from the support layer.

In a first preferred embodiment, the device according to the disclosure furthermore comprises a displacement device. The displacement device is used for in particular horizontally displacing the support layer relative to the at least one die. This makes it possible for a plurality of microstructures to be arranged side-by-side on the support layer. This is achieved such that the support layer and/or the at least one die is displaced, and then, by means of the lifting device, the microstructure, produced in the meantime in the die, is in turn pressed against the support layer and adheres to the support layer via the adhesive layer. It is thereby possible to arrange a plurality of microstructures on the support layer in succession. This results in a patch comprising a plurality of microstructures, in particular microneedle arrays.

In a further preferred embodiment, a plurality of dies are provided side-by-side. These are filled simultaneously or in succession with a corresponding formulation. After corresponding curing, the dies can in particular be displaced simultaneously, by the lifting device, relative to the support layer, such that a plurality of microstructures adhere to the adhesive layer of the support layer, in particular simultaneously, and are demolded by retracting the dies or raising the support layer. It is thereby possible to in particular simultaneously arrange a plurality of individual microstructures on a common support layer, and as a result in turn form a patch comprising a plurality of microstructures.

Preferably, the two above embodiments can be combined with one another, such that a device according to the disclosure both comprises a displacement device, and a plurality of dies are provided side-by-side.

The lifting device can preferably be formed such that, when a plurality of dies are provided, these are displaced or moved simultaneously. In particular, it is preferable for the support layer not to be moved towards the die, but rather for the support layer to be stationary, and the in particular plurality of dies to be pushed against the support layer using a common lifting device. This is carried out in particular from below, against the support layer, the adhesive layer of which faces in the direction of the dies.

In a preferred development, the lifting device preferably comprises one plunger per die. If just one single die is provided, the lifting device comprises just one plunger. In the case of a plurality of plungers, these are preferably interconnected for example by means of a base element, and can thus be moved simultaneously by the lifting device. The plungers are in each case arranged in a receiving device, wherein the receiving device is formed in particular as a hollow cylinder and surrounds the plungers. The receiving device supports the die. In a receiving device formed as a hollow cylinder, a die produced from a resilient material, in particular silicone, is pulled over an opening of the receiving device, and connected thereto in particular in an edge region. The die can be moved away from the receiving device by means of the plunger arranged inside the receiving device. This is possible on account of the resilient die, such that this continues to remain connected to the edge region of the receiving device. This movement makes it possible for the microstructure, produced in the die, to be pushed against the adhesive layer of the support layer in a simple manner.

In a preferred development of the disclosure, the at least one plunger comprises a flat upper surface. This preferably rests on a lower surface of the die when the microstructure is produced by metering the formulation. After the drying of the formulation, and thus a finally formed microstructure, elastic deformation of the die and a corresponding movement of the microstructure in the direction of the support layer can take place by means of further movement of the at least one plunger.

Preferably a plurality of plungers are provided, which are for example interconnected at the base element and can be moved together.

In a preferred embodiment, the method according to the disclosure for producing a patch comprising a plurality of microstructures is carried out by means of the device described above, in particular according to the preferred developments. According to the disclosure, in a first step a formulation is metered into depressions of at least one die. The formulation is in particular liquid containing an active agent. Depending on the production and design of the microstructure, a plurality of liquids can be metered in succession, such that a two-layer or multi-layer structure results. In this case, in particular a top layer does not comprise any active agent.

Subsequently, the at least one die is moved relative to a support layer. The support layer comprises an adhesive layer, against which the microstructure is pressed, such that the microstructure adheres to the support layer. The support layer is preferably stationary, and only the at least one die is moved in the direction of the support layer.

In the next step, an in particular horizontal displacement of the support layer relative to the at least one die can take place, wherein the above-described step of moving the at least one die relative to the support layer is then repeated, in order to arrange at least one further microstructure beside the microstructure already adhering to the support layer.

Alternatively or in addition, a plurality of dies can be provided, which are moved simultaneously.

Patches comprising a plurality of microstructures are produced in particular by repeatedly carrying out the method steps.

In a preferred development of the method, at least one plunger is pushed into a receiving device which is preferably formed as a hollow cylinder. The receiving device retains the die. In this case, the at least one plunger is pushed in such that an upper surface of the plunger rests on the lower surface of the die. After the metering of the formulation, the die can then be moved in the direction of the support layer, using the same plunger. Preferably, in this case, plungers as described above with reference to the device according to the disclosure are interconnected and can be moved simultaneously. Irrespective of whether an individual plunger or a plurality of plungers are moved simultaneously, this preferably results in elastic deformation of the die retained by the receiving device.

Advantageous developments of the method according to the disclosure are described above, together with the device according to the disclosure.

BRIEF DESCRIPTION OF THE DRAWINGS

The disclosure will be explained in greater detail in the following on the basis of a preferred embodiment, with reference to the accompanying drawings, in which.

DETAILED DESCRIPTION

Figure 1:
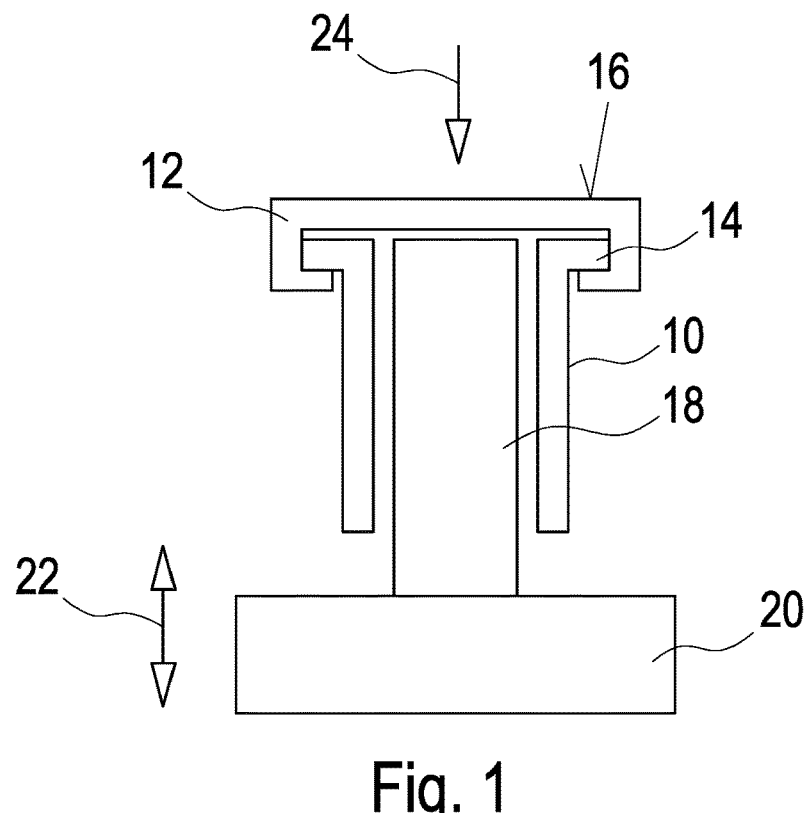
FIG. 1 is a schematic, highly simplified sectional view of a device according to the disclosure in a first position.

In an embodiment shown in simplified form, the device according to the disclosure comprises a receiving device 10 formed as a hollow cylinder. The receiving device is used for receiving a die 12. For this purpose, the receiving device comprises an annular projection or collar 14 at the upper end thereof. This is encompassed by the die 12 such that the die 12 is pulled over the collar 14. The die 12 comprises, on an upper surface 16 thereof, a plurality of in particular pyramid-shaped depressions (not shown). These serve to form the needles of the microstructure.

A plunger 18 is arranged inside the hollow cylinder 10. The plunger 18 is connected to a lifting device 20, in order to be able to be moved horizontally in the direction of an arrow 22, in the embodiment shown. In a first step, in order to produce the microstructure, in particular the microneedle array, as indicated by an arrow 24 a formulation, i.e. a liquid containing an active agent, is metered onto the upper surface 16 of the die 12. Optionally a plurality of liquids, which each comprise an active agent only in part, can be metered onto the upper surface 16 of the die 12 in order to form a plurality of layers. Subsequently, the liquid is dried, such that the corresponding microstructure is formed.

Figure 2:
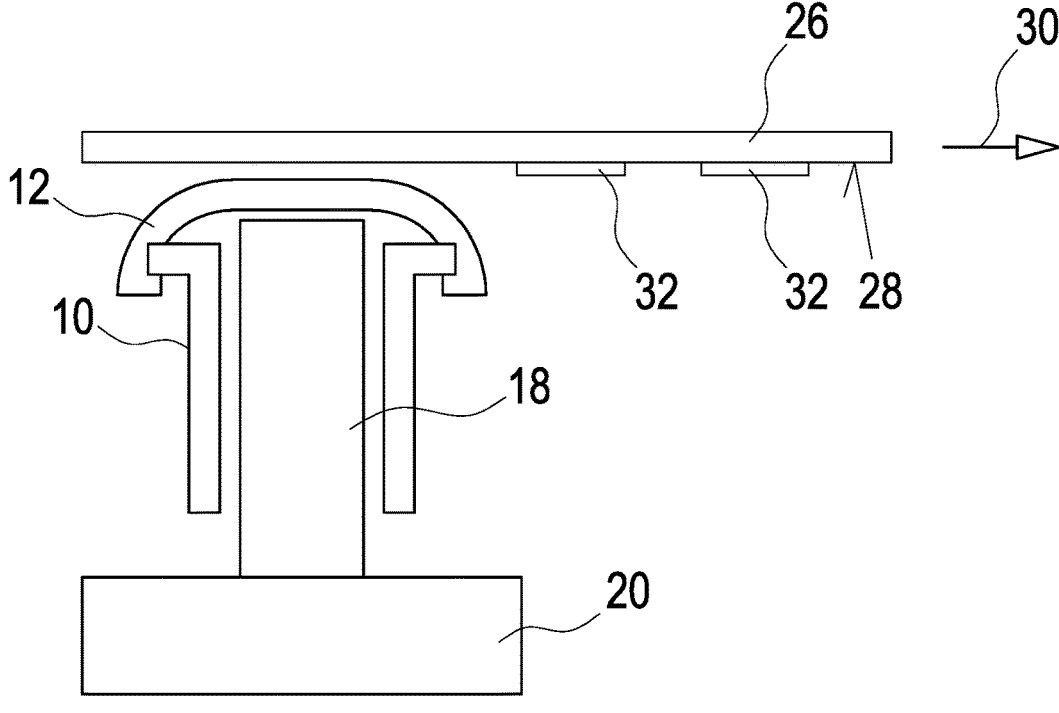
FIG. 2 shows the device shown in FIG. 1 in a second position.

By means of the lifting device 20, as shown in FIG. 2, the die 12 is deformed elastically and moves in the direction of a support layer 26. The support layer 26 comprises an adhesive layer on a lower surface 28. The plunger 18 is moved, by means of the lifting device 20, such that the microneedle array formed in the die is pressed against the adhesive layer. After retraction of the plunger downwards in FIG. 2, on account of the elastic deformation the die also returns into the position shown in FIG. 1. This results in demolding of the microneedle array. Said array adheres to the support layer 16 on account of the provision of the adhesive layer. Following retraction of the plunger 18 and the corresponding demolding of the microneedle array, in the embodiment shown the support layer is moved in the direction of an arrow 30 by means of a displacement device (not shown), such as a conveyor belt. Two microneedle arrays 32 which adhere to the lower surface 28 of the support layer 16 are shown schematically thereon. Since a plurality of microneedle arrays 32 thus adhere to the adhesive layer of the support layer 26, a corresponding patch is formed.

The displacement device can be formed such that the support layer 26 can be displaced not only linearly, in the direction of the arrow 30, but rather also perpendicularly to the drawing plane. It is thus possible to arrange a plurality of rows or groups of microneedle arrays 32 on the support layer.

It is furthermore possible for a group comprising a plurality of devices, as shown in FIG. 1, to be provided. This then comprises a plurality of dies 12 which are arranged side-by-side. The individual plungers 18 of said plurality of devices can be interconnected by means of a base element or a common lifting device 20. It is thus possible to then elastically deform a plurality of dies simultaneously in accordance with the position shown in FIG. 2, and thus simultaneously arrange a plurality of microneedle arrays on the adhesive layer of the support layer. A corresponding group of a plurality devices constructed according to the device shown in FIG. 1 can comprise devices arranged in a plurality of rows, lines or otherwise, such that a group of this kind optionally already comprises all the microneedle arrays of a patch.

The invention claimed is:

1. A device for producing a patch which comprises multiple microstructures, the device comprising:
   at least one die which comprises a plurality of depressions for producing a microstructure;
   a support layer which comprises an adhesive layer; and
   a lifting device comprising one plunger per each die of the at least one die such that the lifting device has at least one plunger that is displaceable in the direction of the support layer,
   wherein each plunger comprises an upper surface which rests on a lower surface of each plunger's respective die of the at least one die,
   wherein the lifting device is configured to move each plunger of the at least one plunger against each respective die of the at least one die so as to perform a relative movement between the at least one die and the support layer such that the microstructure arranged in the at least one die adhere to the support layer, and
   wherein a displacement device for horizontally displacing the support layer relative to the at least one die is provided, such that multiple microstructures are arranged side-by-side on the support layer, and/or multiple dies are provided side-by-side.

2. The device according to claim 1, wherein the lifting device is formed such that multiple microstructures can be moved simultaneously.

3. The device according to claim 1, wherein the at least one plunger is surrounded in each case, at least in part, by a receiving device, and wherein the receiving device supports the at least one die.

4. The device according to claim 3, wherein the at least one plunger can be displaced in the receiving device, and the at least one die is produced from resilient material.

5. The device according to claim 3, wherein the receiving device comprises a hollow cylinder which is connected to a base element.

6. The device according to claim 5, wherein two or more plungers are provided, and wherein the two or more plungers are interconnected by means of the base element.

7. A method for producing a patch comprising multiple microstructures using a device for producing a patch which comprises multiple microstructures, the device comprising:
   at least one die which comprises a plurality of depressions for producing a microstructure;
   a support layer which comprises an adhesive layer; and
   a lifting device for performing a relative movement between the at least one die and the support layer such that the microstructure arranged in the at least one die adhere to the support layer,
   wherein a displacement device for in particular horizontally displacing the support layer relative to the at least one die is provided, such that multiple microstructures are arranged side-by-side on the support layer, and/or multiple dies are provided side-by-side
   wherein the method comprises the steps of:
   metering a formulation into depressions of at least one die;
   moving the at least one die relative to a support layer comprising an adhesive layer, such that the microstructure arranged in the at least one die adheres to the support layer;
   displacing the at least one die relative to the support layer and subsequently moving the at least one die relative to the support layer comprising the adhesive layer, such that the microstructure arranged in the at least one die adheres to the support layer next to the microstructure(s) already adhering thereto;
   pushing at least one plunger into at least one receiving device, wherein, in each case, the receiving device is formed as a hollow cylinder, such that an upper surface of the at least one plunger rests on a lower surface of each respective die of the at least one die and/or
   simultaneously moving multiple dies relative to the support layer comprising the adhesive layer.

8. The method according to claim 7, wherein the at least one die is moved relative to the support layer, in that each respective plunger of the least one plunger is moved further, and wherein the at least one die undergoes elastic deformation.

* * * * *